United States Patent [19]

Maerkl et al.

[11] Patent Number: 4,724,241

[45] Date of Patent: Feb. 9, 1988

[54] PREPARATION OF ETHYLENE GLYCOL

[75] Inventors: Robert Maerkl, Fussgoenheim; Wolfgang Harder, Weinheim, both of Fed. Rep. of Germany

[73] Assignee: BASF Aktiengesellschaft, Ludwigshafen, Fed. Rep. of Germany

[21] Appl. No.: 42,158

[22] Filed: Apr. 24, 1987

[30] Foreign Application Priority Data

May 10, 1986 [DE] Fed. Rep. of Germany ....... 3615835

[51] Int. Cl.$^4$ .............................................. C07C 27/06
[52] U.S. Cl. ..................................... 518/701; 502/152
[58] Field of Search ......................................... 518/701

[56] References Cited

U.S. PATENT DOCUMENTS 4,224,235  9/1980  Beisner et al. ...................... 518/701
4,600,726  7/1986  Bertleff et al. ...................... 518/701

FOREIGN PATENT DOCUMENTS 12924  5/1982  European Pat. Off. .
 1565979  4/1980  United Kingdom .

Primary Examiner—Howard T. Mars
Attorney, Agent, or Firm—John H. Shurtleff

[57] ABSTRACT

Ethylene glycol is prepared from carbon monoxide and hydrogen in a homogeneous liquid phase under superatmospheric pressure and at elevated temperatures in the presence of a rhodium-containing catalyst and in the presence of a porphyrin as organic nitrogen-containing promoter.

9 Claims, No Drawings

PREPARATION OF ETHYLENE GLYCOL

The present invention relates to an improved process for preparing ethylene glycol from carbon monoxide and hydrogen in a homogeneous liquid phase under superatmospheric pressure and at elevated temperatures in the presence of rhodium-containing catalysts and in the presence of organic nitrogen-containing promotors.

This direct synthesis of ethylene glycol from carbon monoxide and hydrogen, where methanol and ethanol are obtained as byproducts, among others, is common knowledge (except for the improvement resulting from the invention); see for example European Pat. No. 0,012,924 or German Laid-Open Application DOS No. 2,643,897. The promotors used therein are nitrogen-containing Lewis bases, for example pyridines such as 2-hydroxypyridine or N-alkyl-substituted morpholines.

The ethylene glycol is generally separated from the crude reaction mixture by aqueous extraction. It is here that many of the preferred prior art promotors exhibit the disadvantage of being soluble in aqueous solution, so that the workup presents problems. Furthermore, the stability of the complexes formed from catalyst metal and promotor leaves something to be desired, in particular at low pressures.

It is an object of the present invention to provide a novel promotor for the direct synthesis of ethylene glycol which stabilizes and at the same time activates the rhodium-containing homogeneous catalyst and is substantially insoluble in water, so that there are no problems in working up. As a consequence of the stabilization of the catalyst system, it should be possible to reuse it for further reactions without loss of productivity.

We have found that this object is achieved with a process for preparing ethylene glycol from carbon monoxide and hydrogen in a homogeneous liquid phase under superatmospheric pressure and at elevated temperatures in the presence of a rhodium-containing catalyst and in the presence of an organic nitrogen-containing promotor, which comprises using a porphyrin as promotor.

Examples of suitable porphyrins are compounds of the general formula I

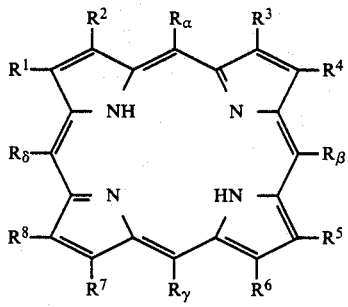

where $R_\alpha$, $R_\beta$, $R_\gamma$ and $R_\delta$ are each hydrogen, alkyl, cycloalkyl, aryl, aralkyl or heterocyclic, $R^1$, $R^2$, $R^3$, $R^4$, $R^5$, $R^6$, $R^7$ and $R^8$ are each hydrogen, alkyl, alkenyl, cycloalkyl, aryl, aralkyl or heterocyclic, and pairs of adjacent radicals on a pyrrole unit can also be bonded to one another to form a 5- or aromatic or nonaromatic 6-ring. The organic radicals can additionally carry substituents which are inert under the reaction conditions; for technical reasons it is advisable to choose substituents which are not very hydrophilic, for example $C_1$–$C_4$-alkoxy.

Alkyl is advantageously of 1 to 20, preferably of 1 to 10, in particular of 1 to 5, carbon atoms, e.g. methyl, ethyl, propyl, isopropyl, butyl, isobutyl, pentyl or isopentyl. Alkenyl is for example vinyl or allyl, and cycloalkyl is for example cyclopentyl or cyclohexyl. A specific example of aryl is phenyl which can be substituted by one or more alkyl, e.g. $C_1$–$C_4$-alkyl. Aralkyl has in particular 7 to 12 carbon atoms, for example benzyl. Heterocyclic denotes in particular nitrogen-containing 5- or 6-membered rings, for example pyridyl.

To facilitate workup and reuse of the porphyrin-stabilized catalyst for a further reaction, it is preferable to use a substantially water-insoluble porphyrin. Owing to their ready accessibility, preference is given to those porphyrins where $R^1$ to $R^8$ are each identical or different alkyl of 1 to 4 carbon atoms, in particular methyl or ethyl, and $R_\alpha$ to $R_\delta$ are each hydrogen, or where $R^1$ to $R^8$ are each hydrogen and $R_\alpha$ to $R_\delta$ are each phenyl, pyridyl or tolyl. Specific examples are octaethylporphyrin, tetramethyltetraethylporphyrin, $\alpha$, $\beta$, $\gamma$, $\delta$-tetraphenylporphyrin and $\alpha$, $\beta$, $\gamma$, $\delta$-tetrapyridylporphyrin.

The porphyrin can be prepared in a conventional manner, for example as described in B. D. Berezin, Coordination Compounds of Porphyrins and Phthalocyanines, John Wiley & Sons, chapter 2, 1981 or Albert Gossauer, Chemie der Pyrrole, Springer Verlag, 1974, page 117/118.

The direct synthesis of ethylene glycol, which proceeds in accordance with the following reaction equation

apart from the novel use of the porphyrin promotor, takes place in a conventional manner, for example as described in earlier German Patent Application No. P 35 32 877.0.

The catalyst used is either rhodium alone or rhodium, in an amount of not less than 5 mol %, together with another carbonyl-forming metal, such as ruthenium, palladium, platinum, iridium, iron, nickel or in particular cobalt.

Since the active carbonyl complexes form spontaneously during the reaction, the catalysts can be used in metallic form or preferably in the form of their salts or complexes such as carbonyl complexes or complexes with, for example, acetylacetone or porphyrin.

Particular preference is given to using the mixed catalysts or catalyst mixtures with rhodium and cobalt as active metals which are described in German Laid-Open Application DOS No. 3,427,138, in which the molar ratio of rhodium:cobalt ranges from about 20:1 to 60:1, in particular from 25:1 to 30:1.

The concentration of rhodium, or, where relevant, the total concentration of carbonyl-forming metals, in the reaction medium is in principle freely choosable, since the concentration essentially has an effect only on the rate of reaction and hence on the space-time yield. Satisfactory space-time yields are in general obtained within the concentration range of 0.01–0.5% by weight of metal; higher concentrations do not yield any significant economic benefits, and when the concentration is lower, for example down to 0.005% by weight, the reaction slows down accordingly.

The total pressure is advantageously within the range of 300–3,000, preferably 600–2,000, bar, the partial pressure of the carbon monoxide preferably ranging from 20 to 80%, in particular from 30 to 60%, of the total pressure.

Good results are obtained at 180°–280° C., the range of 200°–240° C. being generally preferable.

Suitable solvents for the glycol synthesis are the organic solvents known for use in the direct synthesis, such as n- and i-alkanols. Of these solvents, $C_2$–$C_{20}$-n-alkanols, in particular $C_2$–$C_8$-alkanols, preferably the sparingly water-soluble $C_5$–$C_8$-alkanols, are particularly suitable. The addition of compounds such as tetraalkylureas, lactones or N-aryl- or N-alkyl-pyrrolidones or -imidazolidones, in particular N-methylpyrrolide-2-one, 1,5-dimethylpyrrolid-2-one or 1,3-dimethylimidazolid-2-one, can have an advantageous effect on the reaction. The use of solvents of low water-solubility makes it possible to isolate the products of the synthesis, viz. ethylene glycol, methanol and ethanol, from the reaction mixture by simply extracting with water. The substantially water-insoluble porphyrin-stabilized catalyst remains in the organic phase, which is directly reusable for a further glycol synthesis.

The amount of porphyrin preferably ranges from 0.1 to 10 moles, in particular from 0.5 to 5 moles, per mole of central metal. Addition of the porphyrin promotor gives rise to a complex comprising a central atom, for example rhodium or cobalt, with one or more porphyrins as ligands. Instead of preparing the complexes in situ, it is also possible to synthesize them beforehand, for example using the method described by H. Ogoshi et al. in J. Amer. Chem. Soc. 97 (1975), 6461–6465. Advantageously the separately prepared complexes comprise one or more rhodium atoms and in general from 0.5 to 1 porphyrin ligand per central metal.

The reaction can be carried out batchwise or continuously in a conventional manner. The reaction mixture can be worked up by distillation or, advantageously, by extraction with water and subsequent fractionation of the extract phase. The catalyst-containing organic phase which remains after aqueous extraction can be reused for a subsequent reaction batch, so that this procedure is technically particularly highly suitable for continuous operation.

EXAMPLE

A solution of 1.0 g of $Rh(CO)_2$ ($CH_3COCH_2COCH_3$)=0.4 g of Rh, 0.026 g of $Co_2(CO)_8$=0.009 g of Co and 0.11 g of $\alpha$, $\beta$, $\gamma$, $\delta$-tetraphenylporphyrin in 179.0 g of hexan-1-ol and 19.8 g of 1,5-dimethylpyrrolid-2-one was reacted for 5 hours at 230° C. at a total pressure of 1500 bar with an equimolar $CO/H_2$ mixture. The yields, determined by gas chromatography, were:

ethylene glycol: 7.10 g
methanol: 13.5 g
ethanol: 2.7 g

We claim:

1. In a process for preparing ethylene glycol by reacting carbon monoxide and hydrogen in a homogeneous liquid phase under superatmospheric pressure and at elevated temperatures in the presence of a rhodium-containing catalyst and in the presence of an organic nitrogen-containing promotor in an organic solvent, the improvement which comprises carrying out the reaction in the presence of a porphyrin as the promotor.

2. A process as claimed in claim 1, wherein the porphyrin used has the formula I

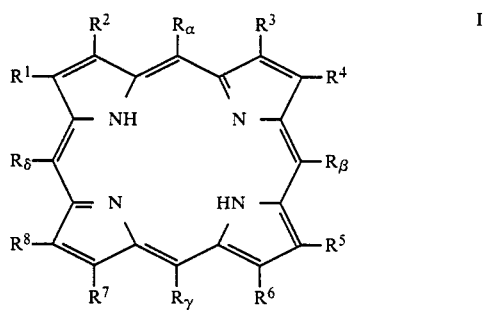

where $R_\alpha$, $R_\beta$, $R_\gamma$ and $R_\delta$ are each hydrogen or alkyl, cycloalkyl, aryl, aralkyl or heterocyclic radicals, $R^1$, $R^2$, $R^3$, $R^4$, $R^5$, $R^6$, $R^7$ and $R^8$ are each hydrogen or alkyl, alkenyl, cycloalkyl, aryl, aralkyl or heterocyclic radicals, and pairs of adjacent radicals of a pyrrole unit can also be bonded to one another to form a 5- or aromatic or nonaromatic 6- ring.

3. A process as claimed in claim 2, wherein, in porphyrin I, $R^1$, $R^2$, $R^3$, $R^4$, $R^5$, $R^6$, $R^7$ and $R^8$ are each alkyl and $R_\alpha$, $R_\beta$, $R_\gamma$ and $R_\delta$ are each hydrogen.

4. A process as claimed in claim 2, wherein, in porphyrin I, $R^1$, $R^2$, $R^3$, $R^4$, $R^5$, $R^6$, $R^7$ and $R^8$ are each hydrogen and $R_\alpha$, $R_\beta$, $R_\gamma$ and $R_\delta$ are each phenyl, pyridyl or tolyl.

5. A process as claimed in claim 1, wherein from 0.1 to 10 moles of porphyrin per mole of metal atom are present in the reaction mixture.

6. A process as claimed in claim 1, wherein the catalyst used is a rhodium/cobalt mixed complex or a mixture of a rhodium and a cobalt complex, with a molar ratio of rhodium:cobalt of from about 20:1 to 60:1.

7. A process as claimed in claim 1, wherein the reaction is carried out under a pressure of from 300 to 3,000 bar, the partial pressure of carbon monoxide ranging from 20 to 80% of the total pressure.

8. A process as claimed in claim 1, wherein the temperature is from 180° to 280° C.

9. A process as claimed in claim 1, wherein the solvent is an n- or i-alkanol.

* * * * *